United States Patent [19]

Schönafinger et al.

[11] 4,332,801
[45] Jun. 1, 1982

[54] 3-AMINOSYDNONIMINES, THEIR PREPARATION AND USE

[75] Inventors: Karl Schönafinger; Rudi Beyerle; Rolf-Eberhard Nitz, all of Frankfurt am Main; Piero A. Martorana, Bad Homburg, all of Fed. Rep. of Germany; Volker Fiedler, Detroit, Mich.

[73] Assignee: Cassella Aktiengesellschaft, Frankfurt am Main, Fed. Rep. of Germany

[21] Appl. No.: 233,054

[22] Filed: Feb. 10, 1981

Related U.S. Application Data

[62] Division of Ser. No. 166,951, Jul. 8, 1980, Pat. No. 4,305,939.

[30] Foreign Application Priority Data

Jul. 28, 1979 [DE] Fed. Rep. of Germany ....... 2930736

[51] Int. Cl.³ .................. C07D 417/04; A61K 31/38; A61K 31/41; C07D 417/14
[52] U.S. Cl. ..................................... 424/246; 544/60; 544/58.7
[58] Field of Search .................. 544/58.7, 60; 424/246

[56] References Cited

U.S. PATENT DOCUMENTS 3,833,580  9/1974  Gotz ............................. 260/247.2 A
3,898,230  8/1975  Regnier ....................... 260/256.4 N

FOREIGN PATENT DOCUMENTS 1219254  1/1971  United Kingdom .

Primary Examiner—John M. Ford
Attorney, Agent, or Firm—Berman, Aisenberg & Platt

[57] ABSTRACT

Physiologically-acceptable 3-aminosyndnonimines of the formula

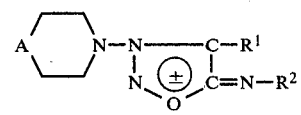

(I)

and their pharmacologically-acceptable acid-addition salts, when formulated into medicament dosage forms, are useful for reducing systemic blood pressure, pulmonary artery pressure and left ventricular end diastolic pressure when orally administered to patients in need of such pressure reduction. These compounds are prepared by cyclizing a compound which, in its free-base state, is of the formula

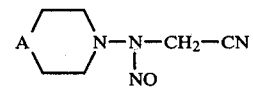

(II)

to a corresponding product which, in its free-base state, is of the formula

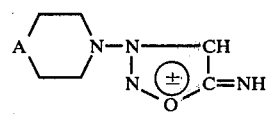

(Ia)

and, when $R^2$ is other than —H, acylating that product.

22 Claims, No Drawings

3-AMINOSYDNONIMINES, THEIR PREPARATION AND USE

CROSS-REFERENCE TO RELATED APPLICATION

The present application is a division of application Ser. No. 166,951, filed July 8th, 1980 now U.S. Pat. No. 4,305,939 issued Dec. 15, 1981.

BACKGROUND

According to "The Merck Index", ninth edition, pages 815 and 816, Merck & Co., Inc., 1976, N-carboxy-3-morpholinosydnonimine ethyl ester (morsydomine) is a member of a class of non-benzene aromatic, heterocyclic and mesoionic type of compounds with stated pharmaceutical indications. Publications are cited therein with regard to developmental work stability studies and pharmacological studies on sydnone imines.

SUMMARY OF THE INVENTION

The invention concerns (a) pharmacologically-active and physiologically-acceptable compounds which, in free-base form, are of formula I:

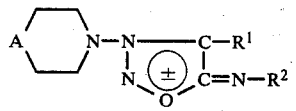

(b) intermediates in the synthesis of such compounds, (c) a method for synthesizing such compounds, (d) medicament compositions based upon such compounds and (e) administration of such compounds or compositions. In formula I, the indicated variables, $R^1$, $R^2$ and A, have the following meanings:

$R^1$ is —H or halo;

$R^2$ is —H, —NO, —$COR^3$ or —$SO_2R^4$;

$R^3$ is —H, optionally-substituted aliphatic hydrocarbyl with from 1 to 6 carbon atoms, cycloaliphatic hydrocarbyl having from 5 to 8 ring carbon atoms, optionally-substituted carbocyclic aryl having from 6 to 12 ring carbon atoms, araliphatic hydrocarbyl with from 7 to 13 carbon atoms, alkoxy with from 1 to 6 carbon atoms, hydrocarbyl aryloxy with from 6 to 12 ring carbon atoms, heterocyclic aryl having a 5- or 6-membered ring or alkoxycarbonyl with from 2 to 7 carbon atoms;

A is >$S(O)_m$ or >N—$SO_2R^5$;

m is 0, 1 or 2; and each of $R^4$ and $R^5$ is, independently, aliphatic hydrocarbyl with from 1 to 6 carbon atoms, carbocyclic aryl with from 6 to 12 ring carbon atoms, mono- or disubstituted carbocyclic aryl with from 6 to 12 ring carbon atoms and in which any substituent is methyl or chloro, or dialkylamino, each alkyl of which has from 1 to 4 carbon atoms;

any substituent of optionally-substituted aliphatic hydrocarbyl being alkoxy having from 1 to 6 carbon atoms or aryloxy having from 6 to 12 carbon atoms;

any substituent of optionally-substituted carbocyclic aryl, which is unsubstituted, monosubstituted, disubstituted or trisubstituted, being a nuclear substituent, which is halo, alkyl with from 1 to 4 carbon atoms or alkoxy with from 1 to 4 carbon atoms; and any hetero ring member of heterocyclic aryl being >N—, —O— or —S—; any heterocyclic aryl having at most one ring oxygen atom, at most one ring sulfur atom, at most three ring nitrogen atoms and at least two ring carbon atoms.

Compounds of formula I and their physiologically-acceptable acid-addition salts are useful in the same manner, with the same mode of administration, substantially similar dosage for the same duration of treatment, as morsydomine and isosorbide dinitrate for patients in need of a coronary vasodilator, e.g. in treating angina pectoris.

Unless otherwise limited, the terms used to define the variables in formula I have the following meansings:

aliphatic—saturated or unsaturated acyclic hydrocarbyl with from 1 to 6 carbon atoms and in which any unsaturation is preferably olefinic unsaturation, e.g. linear or branched-chain alkyl, allyl and 2-buten-1-yl. The aliphatic radical representing $R^3$ is preferably alkyl and, most suitably, alkyl with from 1 to 4 carbon atoms. The aliphatic in the definition of $R^4$ and/or $R^5$ is advantageously alkyl and preferably methyl.

alkoxy—alkyl-oxy in which the alkyl is linear or branched-chain and has from 1 to 6 carbon atoms, e.g. methoxy, ethoxy, isopropoxy, butoxy and hexoxy.

alkoxycarbonyl—in this grouping "alkoxy" has its previously-indicated meaning, thus providing radicals with from 2 to 7 carbon atoms, e.g. methoxycarbonyl, ethoxycarbonyl, isopropoxycarbonyl and amyloxycarbonyl. One of the preferred meanings for $R^3$ is alkoxycarbonyl with a total of 2 or 3 carbon atoms.

alkyl—saturated straight- or branched-chain acyclic hydrocarbyl having from 1 to 4 carbon atoms, e.g. methyl, ethyl, propyl, isopropyl, butyl, secondary butyl and tertiary butyl.

araliphatic—aliphatic hydrocarbyl substituted by carbocyclic aryl and having a total of from 7 to 13 carbon atoms, e.g. α-naphthyl-methyl, β-naphthyl-isopropyl and, preferably, benzyl, phenethyl or styryl.

aryl—a carbocyclic radical having from 5 to 12 ring members and aromatic unsaturation, e.g. phenyl, α-naphthyl or β-naphthyl. When $R^3$ is is preferably phenyl, monosubstituted phenyl, disubstituted phenyl or trisubstituted phenyl.

aryloxy—the "aryl" of aryloxy is carbocyclic aryl having from 6 to 12 carbon atoms; examples of aryloxy are thus phenoxy, α-naphthyloxy and β-naphthyloxy.

carbocyclic—a hydrocarbyl ring or condensed ring system having from 5 to 12 ring members and inclusive of homocyclic aryl having from 6 to 12 ring carbon atoms (e.g. phenyl and α-naphthyl) and a saturated or partially unsaturated cycloaliphatic hydrocarbyl ring having from 5 to 8 ring carbon atoms, e.g. cyclopentyl, cyclooctyl, 2-cyclohexenyl and cyclohexyl, preferably cyclohexyl or cyclopentyl.

carbocyclic aryl—homocyclic aryl having from 6 to 12 ring carbon atoms and comprising a single ring or a condensed-ring system, e.g. phenyl, α-naphthyl and β-naphthyl. When $R^4$ and/or $R^5$ is aryl, each is, independently, preferably phenyl, particularly phenyl substituted in the 4-position by methyl or chloro.

cycloaliphatic—a saturated or partially unsaturated hydrocarbyl ring having from 5 to 8 ring carbon atoms, e.g. cycloheptyl, 2,3-dihydrophenyl and, preferably, cyclohexyl and cycloheptyl.

dialkylamino—dialkylamino wherein each alkyl, independently, has from 1 to 4 carbon atoms and is either straight or branched chained, e.g. diisopropylamino, dibutylamino and ethylmethylamino; each alkyl of dialkylamino is preferably ethyl or methyl.

halo—bromo, chloro, fluoro or iodo. When $R^1$ is halo, it is preferably chloro or bromo.

heterocyclic aryl—a 5- or 6-membered ring radical in which at least one ring member is a nitrogen, an oxygen or a sulfur atom. Such rings have at least two ring carbon atoms, at most one ring oxygen atom, at most one ring sulfur atom and at most three ring nitrogen atoms. Examples of such radicals are: pyrrolyl, imidazolyl, pyrazolyl, pyrazinyl, pyrimidyl, pyridazinyl, thienyl, furyl, thiazolyl, furazanyl, oxazolyl, thiadiazolyl, triazinyl, triazolyl and, preferably, pyridyl.

hydrocarbyl—a radical having one free bond and composed entirely of hydrogen and carbon atoms, e.g. carbocyclic aryl and alkyl.

optionally substituted—the radical to which this expression is applied is either substituted or unsubstituted.

substituent—each radical which is substituted has at least one substituent. Any substituent of optionally-substituted aliphatic hydrocarbyl is alkoxy having from 1 to 6 carbon atoms or aryloxy having from 6 to 12 carbon atoms; any substituent of optionally-substituted carbocyclic aryl is halo, alkyl with from 1 to 4 carbon atoms or alkoxy with from 1 to 4 carbon atoms. In the definition of $R^4$ and $R^5$ substituents of carbocyclic aryl are limited to one or two, which are, independently, methyl or chloro, e.g., 4-methylphenyl, 4-chlorophenyl, 2-chloro-4-methylphenyl, 2,4-dimethylphenyl and 2,4-dichlorophenyl. When $R^3$ is aliphatic, particularly alkyl, and is substituted by an alkoxy substituent, the alkoxy is preferably one having from 1 to 4 carbon atoms, e.g. methoxy, ethoxy and isopropoxy. When $R^3$ is substituted aryl, preferably substituted phenyl, substitution is by one, two, or three radicals, each of which, independently, is preferably chloro, methyl, methoxy or ethoxy.

substituted—a subject radical which bears a substituent as hereinbefore defined. In the definition of $R^3$ aliphatic hydrocarbyl and carbocyclic aryl optionally bear substituents. Also, the carbocyclic aryl of each of $R^4$ and $R^5$ is, optionally, monosubstituted or disubstituted. Any ring substitution is preferably at positions at which such substituents are normally attracted.

$R^1$ is preferably —H. Further preferred compounds are those wherein $R^2$ is —H, especially when $R^1$ is —H and/or A is $>SO_2$, as well as those wherein $R^3$ is alkoxy with one or two carbon atoms or alkoxycarbonyl with a total of two or three carbon atoms. Moreover, the compounds of the present invention, and apparent from the table on page 14 are also preferred.

Compounds of formula I are prepared, e.g., by cyclizing a compound of formula II

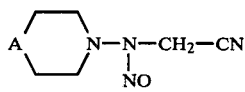

(II)

to obtain a compound of formula Ia

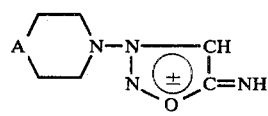

(Ia)

and, for those compounds in which $R^2$ is other than —H, subjecting the thus-obtained compound Ia to acylation (with an appropriate acylating agent to introduce the radical —$COR^3$ or —$SO_2R^4$) or to nitrosation (with nitrous acid) and/or, in order to introduce halogen, to reaction with a halogen or with a halogenating agent. The resulting compound is then optionally converted to an acid-addition salt by conventional established techniques.

The cyclization of compound II to compound Ia is carried out in a suitable inorganic or organic solvent [for example water or an alkanol with 1 to 4 C atoms (e.g. methanol and ethanol), a carboxylic acid alkyl ester (e.g. methyl propionate) or a mixture of such solvents, such as water/methanol or, preferably, ethyl acetate/methanol] with the addition of a cyclizing agent, usually at temperatures of from 0° to 40° C. and preferably of from 0° to 20° C. Suitable cyclizing agents are those which give a pH value below 3 in aqueous solution; these include, e.g., mineral acids (such as hydrochloric acid, sulfuric acid, nitric acid and phosphoric acid) and strong organic acids (such as trifluoroacetic acid). On cyclization, the corresponding acid-addition salt of compound Ia is obtained.

Compounds Ia are those according to the invention in which, according to formula I, $R^1$ and $R^2$ denote hydrogen. In order to introduce the —NO group ($R^2$ is —NO), compound Ia is conventionally nitrosated. To introduce —$COR^3$ or —$SO_2R^4$ (as $R^2$), compound Ia is acylated with a suitable acylating agent of one of formulae III and IV:

wherein X denotes, for example, halo (particularly chloro), —$OCOR^3$, —O-aryl (particularly tolyloxy), nitrophenyloxy or dinitrophenyloxy.

The nitrosation is carried out in a suitable solvent, preferably water, in a manner known per se and at temperatures of 0° to 10° C. Normally, the nitrous acid is produced from an alkali metal nitrite and hydrochloric acid. It is appropriate to adjust the aqueous solution of the compound Ia with hydrochloric acid to a pH value of 1 to 3 and to add the alkali metal nitrite dropwise to the stirred and cooled solution of the compound in the form of an aqueous solution.

Acylation with the acylating agent III or IV is effected with stirring in a suitable solvent, such as water, a polar organic solvent (such as dimethylformamide, dimethylsulfoxide or pyridine) or an excess of the acylating agent (optionally in the presence of an acid-binding agent, such as pyridine or sodium bicarbonate) at temperatures of from 0° C. up to boiling point of the solvent or acylating agent and preferably at from 0° to 20° C. When $R^1$ is a halogen atom, it is introduced by reacting a compound Ia or, preferably, a compound Ib

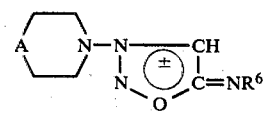

(Ib)

(in which $R^6$ denotes —NO, —$COR^3$ or —$SO_2R^4$) with a suitable conventional halogenating agent. This reaction is conventionally carried out in a suitable solvent, such as a chlorinated hydrocarbon (e.g. carbon tetrachloride) or glacial acetic acid, at temperatures of from 0° to 20° C. The halogenating agents used are, for example, halosuccinimides or elementary halogens. If desired, the —$COR^3$ or —$SO_2R^4$ radical representing $R^6$ is split off by hydrolysis in an acid medium in a manner which is in itself known from the compound obtained by halogenation of compound Ib. Compounds I (according to the invention) in which $R^1$=halogen and $R^2$=hydrogen are obtained in this way.

Substituted 3-amino-sydnonimines of formula I form acid-addition salts with inorganic or organic acids. Such acids are, for example, hydrochloric acid, hydrobromic acid, phosphoric acid, sulfuric acid, oxalic acid, lactic acid, tartaric acid, acetic acid, salicyclic acid, benzoic acid, citric acid, ascorbic acid, adipic acid and naphthalenedisulfonic acid. Frequently, the acid-addition salts, particularly the hydrochlorides, of compounds of formula I are obtained directly in the synthesis of compounds of formula I. If desired, the free-base compounds of formula I are conventionally obtained from the acid-addition salts by dissolving or suspending the salts in water and rendering the solution or suspension alkaline, for example, with aqueous sodium hydroxide solution, and then isolating the free base. Pharmacologically-acceptable salts are preferred.

The required starting compounds of formula II which are prepared by the Strecker aminonitrile synthesis from compounds of formula V

(V)

by reaction with formaldehyde and hydrocyanic acid in a suitable solvent, such as water; in this reaction a compound of formula VI

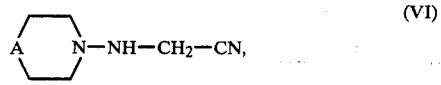

(VI)

which forms first, is converted to compound II by nitrosation with nitrous acid. The nitrosation is carried out in known manner in a suitable solvent, preferably water, at temperatures of from 0° to 10° C. The nitrous acid is usually produced from an alkali-metal nitrite, e.g. sodium nitrite, and hydrochloric acid. It is advantageous to adjust the pH value of the aqueous solution of compound VI to 1 to 3 with hydrochloric acid and to add the alkali-metal nitrite dropwise, in the form of an aqueous solution, to the stirred and cooled solution of the compound.

The solution of the resulting compound II is optionally subjected to a direct cyclization reaction. Usually, however, it is appropriate to take up the nitroso compound II in a suitable organic solvent first and to carry out the cyclization to a compound of formula I in such solvent, optionally after adding a further solvent.

Some compounds of formula V are known; all are synthesized, e.g., by the method illustrated in the examples for the preparation of 1-amino-4-methylsulfonylpiperazine, in which method the piperazine VII is first reacted with potassium cyanate to obtain the urea VIII, which is reacted by a Hoffman's degradation to produce the compound IIa.

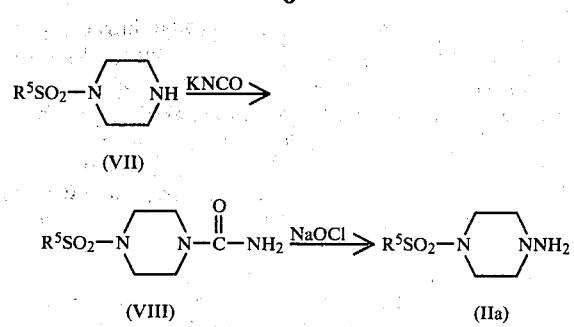

Compounds according to the invention of formula Ic:

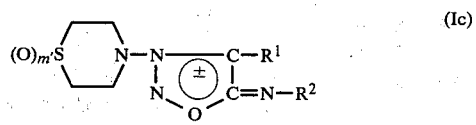

(Ic)

in which m′ is 1 or 2 are optionally prepared by oxidation of compounds (according to the invention) of formula Id

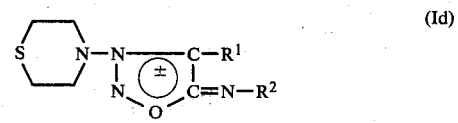

(Id)

This oxidation is advantageously carried out with hydrogen peroxide in a suitable solvent, for example glacial acetic acid, at room temperature (about 20° C.) or at a slightly elevated temperature.

All starting compounds required for the synthesis of physiologically-acceptable compounds of formula I and their acid-addition salts are known and available or are readily prepared from known compounds by conventional procedures.

Compounds of formula I and their pharmacologically-acceptable acid-addition salts possess valuable pharmacological properties. Their action on the cardiovascular system is particularly pronounced. Compared to the commercially available compound morsydomine of similar structure or the commercially available compound isosorbide dinitrate (ISDN) exhibiting similar action, they display, with respect to some properties, a stronger action and/or have a longer duration of action. They lower the systemic blood pressure, the pulmonary artery pressure and the left ventricular end diastolic pressure, thus reducing cardiac work (in the sense of an anti-anginal action) without provoking reflex tachycardia.

The anti-anginal action of compounds according to the invention is measured, e.g., using the following method:

The investigations were carried out on mongrel dogs of both sexes under pentobarbital anesthesia (30 to 40 mg/kg administered intravenously) or under urethane-chloralose anesthesis (3 ml/kg or urethane/chloralose mixture administered intravenously=20 mg/kg of chloralose and 250 mg/kg of urethane). Artificial respiration of the animals was carried out using a Bird Mark 7 respirator. The expiratory carbon dioxide content (measured with a Uras) was between 4.5 and 5% by volume. The animals under pentobarbital anesthesia were given a continuous infusion of pentobarbital intravenously (vena cephalica)=4 mg/kg/6 ml/hour during the entire experiment in order to insure a constant depth of anesthesis; the animals under urethane/chloralose anesthesia were given no infusion. The preparation of the test animal was followed by a stabilization period of about 1 hour until all of the haemodynamic parameters were in the steady state. The experiment proper was then started.

The systolic and diastolic blood pressure was measured peripherally in the arteria femoralis via a Statham pressure reactor. A Millar tip catheter inserted via the arteria carotis into the left ventricle provided the signal for the LVEDP (left ventricular end diastolic pressure) and the heart rate. The mean blood pressure in the arteria pulmonalis was detected by means of a second tip catheter inserted via the vena jugularis.

With this methodology the following compounds according to the invention were administered intravenously (vena cephalica) and confirmed significant activity in the indicated dosages:

A = 3-tetrahydro-1,4-thiazin-4-yl 1,1-dioxide)sydnonimine hydrochloride
B = $N^6$-cyclohexylcarbonyl-3-(tetrahydro-1,4-thiazin-4-yl 1,1-dioxide)sydnonimine
C = 3-(4-methanesulfonyl-piperazin-1-yl)sydnonimine hydrochloride
D = $N^6$-ethoxycarbonylcarbonyl-3-(4-methanesulfonyl-piperazin-1-yl)sydnonimine
E = $N^6$-benzoyl-3-(4-methanesulfonyl-piperazin-1-yl)sydnonimine
F = 3-(4-dimethylaminosulfonyl-piperazin-1-yl)sydnonimine hydrochloride
G = $N^6$-(4-chlorobenzoyl)-3-(tetrahydro-1,4-thiazin-4-yl1,1-dioxide)sydnonimine
H = 3-(thiomorpholino)sydnonimine hydrochloride and
I = $N^6$-propionyl-3-(4-dimethylaminosulfonyl-piperazin-1-yl)sydnonimine hydrochloride active compound of formula I or an acid-addition salt thereof, comprise preservative, stabilizer, emulsifier, buffer substance and, optionally, one or more further therapeutically-active substances. Further therapeutically-active substances of this type are, for example, β-receptor blockers (such as propranolol, pindolol and metoprolol), vasodilators (such as carbochromen), tranquilizers (such as barbituric acid derivatives, 1,4-benzodiazepines and meprobamate), diuretics (such as chlorothiazide), agents which tonicize the heart (such as digitalis preparations), hypotensive agents (such as hydralazine, dihydralazine, prazosin, clonidine and Rauwolfia alkaloids), agents which lower the level of fatty acid in the blood (such as bezafibrate and fenofibrate) and agents for the prophylaxis of thrombosis (such as phenprocoumon).

The pharmaceutical formulations contain, e.g., 0.1 to 50 mg and, preferably, from 0.5 to 10 mg/dose. The daily dosage range per kilogram of bodyweight is e.g. 0.001 to 1 mg, preferably 0.005 to 0.2 mg.

Further illustrative of similarly useful compounds of formula I (prepared by analogy processes from equivalents of corresponding starting materials) are each of the following and their acid-addition salts, e.g. the hydrochloride of each:

3-(4-phenylsulfonyl-piperazin-1-yl)sydnonimine
4-bromo-3-(tetrahydro-1,4-thiazin-4-yl 1-oxide)sydnonimine
4-chloro-3-(tetrahydro-1,4-thiazin-4-yl 1,1-dioxide)sydnonimine
4-bromo-3-(4-phenylsulfonyl-piperazin-1-yl)sydnonimine
4-chloro-3-(4-tosyl-piperazin-1-yl)sydnonimine
4-bromo-3-(4-dimethylaminosulfonyl-piperazin-1-yl)sydnonimine
$N^6$-nitroso-3-thiomorpholinosydnonimine
$N^6$-nitroso-3-(tetrahydro-1,4-thiazin-4-yl 1-oxide) sydnonimine

| Substance | Dose mg/kg | LVEDP ΔmmHg | PAP t/min | PAP ΔmmHg | BPm t/min | BPm ΔmmGH | HR t/min | HR Δb/min | t/min |
|---|---|---|---|---|---|---|---|---|---|
| MOR | 0.05 | −3.5 | 90 | −2.1 | 90 | −6 | 60 | +7 | 90 |
| ISDN | 0.05 | −2.1 | 30 | −0.7 | 20 | −19 | 15 | ±0 | 0 |
| A | 0.05 | −4.9 | 80 | −3.1 | 40 | −61 | 90 | +8.75 | 70 |
| B | 0.05 | −2.5 | 90 | −7.5 | 60 | −27.5 | 60 | ±0 | 0 |
| C | 0.05 | −2.3 | 25 | −1.2 | 20 | −32 | 45 | +6.7 | 40 |
| D | 0.05 | −3 | 95 | −4 | 95 | −20 | 75 | +5 | 20 |
| E | 0.05 | −3 | >120 | −3 | >120 | −20 | >120 | ±0 | 0 |
| F | 0.05 | −4 | 40 | −3 | 50 | −10 | 25 | +10 | 10 |
| G | 0.05 | −6 | >90 | −2 | >90 | −35 | 90 | +10 | >90 |
| H | 0.05 | −5 | 75 | −3.1 | 70 | −31 | 60 | +7.5 | 40 |
| I | 0.05 | −3.5 | >90 | −1.7 | 60 | −26 | 90 | +2.5 | 30 |

PAP = mean pulmonary artery pressure
LVEDP = left ventricular end diastolic pressure
BPm = mean peripheral blood pressure
HR = heart rate
t/min = duration of activity (mean)
ISDN = isosorbide dinitrate (reference substance)
MOR = morsydomine (reference substance)

For use in therapy, a pharmacologically-acceptable acid-addition salt of a subject compound or a subject compound in free-base form is mixed with customary pharmaceutical filler or excipient, tabletting agents, disintegrators, binders, lubricants, thickeners or diluents, solvents or solubilizing agents or agents used to obtain a depot effect, the additives being those which make the resulting formulation suitable for enteral or parenteral administration. Appropriate pharmaceutical formulations are, for example, tablets, sugar-coated tablets, pills, capsules, solutions, suspensions or emulsions which, in addition to an effective amount of an $N^6$-nitroso-3-(tetrahydro-1,4-thiazin-4-yl 1,1-dioxide)-sydnonimine
$N^6$-nitroso-3-(4-methanesulfonyl-piperazin-1-yl)sydnonimine
$N^6$-nitroso-3-(4-phenylsulfonyl-piperazin-1-yl)sydnonimine
$N^6$-nitroso-3-[4-p-chlorophenylsulfonyl)piperazin-1-yl]sydnonimine
$N^6$-nitroso-3-[4-(N-ethyl-N-methylaminosulfonyl)piperazin-1-yl]-sydnonimine N⁶-nitroso-4-bromo-3-(tetrahydro-1,4-thiazin-4-yl 1-oxide)sydnonimine
N⁶-nitroso-4-chloro-3-(tetrahydro-1,4-thiazin-4-yl 1,1-dioxide)sydnonimine
N⁶-nitroso-4-bromo-3-(4-ethanesulfonyl-piperazin-1-yl)sydnonimine
N⁶-nitroso-4-chloro-3-[4-(2,4-dichlorophenylsulfonyl)-piperazin-1-yl]sydnonimine
N⁶-nitroso-4-bromo-3-(4-diethylaminosulfonyl-piperazin-1-yl)sydnonimine
N⁶-formyl-3-thiomorpholinosydnonimine
N⁶-formyl-3-(tetrahydro-1,4-thiazin-4-yl 1-oxide)sydnonimine
N⁶-formyl-3-(4-ethanesulfonyl)piperazin-1-yl)sydnonimine
N⁶-formyl-3-[4-(2,4-dimethylphenylsulfonyl)piperazin-1-yl]sydnonimine
N⁶-formyl-3-(4-dimethylaminosulfonyl-piperazin-1-yl)sydnonimine
N⁶-formyl-4-chloro-3-(tetrahydro-1,4-thiazin-4-yl 1-oxide)sydnonimine
N⁶-formyl-4-bromo-3-(tetrahydro-1,4-thiazin-4-yl 1,1-dioxide)sydnonimine
N⁶-formyl-4-chloro-3-(4-methanesulfonyl-piperazine-1-yl)sydnonimine
N⁶-formyl-4-chloro-3-(4-phenylsulfonyl-piperazin-1-yl)sydnonimine
N⁶-formyl-4-bromo-3-[4-(4-chloro-o-tolylsulfonyl)piperazin-1-yl]sydnonimine
N⁶-formyl-4-chloro-3-(4-dimethylaminosulfonyl-piperazin-1-yl)sydnonimine
N⁶-acetyl-3-(tetrahydro-1,4-thiazin-4-yl 1-oxide)sydnonimine
N⁶-propionyl-3-(4-phenylsulfonyl-piperazin-1-yl)sydnonimine
N⁶-butyryl-3-[4-(p-chlorophenylsulfonyl)piperazin-1-yl]sydnonimine
N⁶-propionyl-4-bromo-3-(tetrahydro-1,4-thiazin-4-yl 1-oxide)sydnonimine
N⁶-acetyl-4-chloro-3-(tetrahydro-1,4-thiazin-4-yl 1,1-dioxide)sydnonimine
N⁶-acetyl-4-bromo-3-(4-ethanesulfonyl-piperazin-1-yl)sydnonimine
N⁶-propionyl-4-chloro-3-[4-(2,4-dichlorophenylsulfonyl)piperazin-1-yl]sydnonimine
N⁶-acetyl-4-bromo-3-(4-diethylaminosulfonyl-piperazin-1-yl)sydnonimine
N⁶-methoxyacetyl-3-thiomorpholinosydnonimine
N⁶-phenoxypropionyl-3-(tetrahydro-1,4-thiazin-4-yl 1-oxide)sydnonimine
N⁶-ethoxybutyryl-3-(tetrahydro-1,4-thiazin-4-yl 1,1-dioxide)sydnonimine
N⁶-phenoxyacetyl-3-(4-methanesulfonyl-piperazin-1-yl)sydnonimine
N⁶-methoxypropionyl-3-(4-phenylsulfonyl-piperazin-1-yl)sydnonimine
N⁶-ethoxyacetyl-3-[4-(N-ethyl-N-methylaminosulfonyl)piperazin-1-yl]sydnonimine
N⁶-methoxypropionyl-4-bromo-3-(tetrahydro-1,4-thiazin-4-yl 1-oxide)sydnonimine
N⁶-ethoxypropionyl-4-chloro-3-(tetrahydro-1,4-thiazin-4-yl 1,1-dioxide)sydnonimine
N⁶-phenoxyacetyl-4-bromo-3-(4-ethanesulfonyl-piperazin-1-yl)sydnonimine
N⁶-phenoxybutyryl-4-chloro-3-[4-(2,4-dichlorophenylsulfonyl)-piperazin-1-yl]sydnonimine
N⁶-methoxybutyryl-4-bromo-3-(4-diethylaminosulfonyl-piperazin-1-yl)sydnonimine
N⁶-cyclopentylcarbonyl-3-thiomorpholinosydnonimine
N⁶-cyclohexylcarbonyl-3-(tetrahydro-1,4-thiazin-4-yl 1-oxide)sydnonimine
N⁶-cycloheptylcarbonyl-3-[4-(p-chlorophenylsulfonyl)-piperazin-1-yl]sydnonimine
N⁶-cyclohexylcarbonyl-4-bromo-3-(tetrahydro-1,4-thazin-4-yl 1-oxide)sydnonimine
N⁶-(2-cyclohexenyl)carbonyl-4-bromo-3-(4-ethanesulfonyl-piperazin-1-yl)sydnonimine
N⁶-cycloheptylcarbonyl-4-fluoro-3-[4-(α-naphthylsulfonyl)-piperazin-1-yl]sydnonimine
N⁶-cyclopentylcarbonyl4-chloro-3-[4-(2,4-dichlorophenylsulfonyl)piperazin-1-yl]sydnonimine
N⁶-cyclohexylcarbonyl-4-bromo-3-(4-diethylaminosulfonyl-piperazin-1-yl)sydnonimine
N⁶-benzoyl-3-thiormorpholinosydnonimine
N⁶-(α-naphthyl)carbonyl-3-(tetrahydro-1,4-thiazin-4-yl 1-oxide)sydnonimine
N⁶-benzoyl-3-(4-phenylsulfonyl-piperazin-1-yl)sydnonimine
N⁶-(β-naphthyl)carbonyl-3-[4-(p-chlorophenylsulfonyl)piperazin-1-yl]sydnonimine
N⁶-(α-naphthyl)carbonyl-4-bromo-3-(tetrahydro-1,4-thiazin-4-yl 1-oxide)sydnonimine
N⁶-benzoyl-4-chloro-3-(tetrahydro-1,4-thiazin-4-yl 1,1-dioxide)sydnonimine
N⁶-(β-naphthyl)carbonyl-4-bromo-3-(4-ethanesulfonyl-piperazin-1-yl)sydnonimine
N⁶-(α-naphthyl)carbonyl-4-chloro-3-[4-(2,4-dichlorophenylsulfonyl)piperazin-1-yl]sydnonimine
N⁶-benzoyl-4-bromo-3-(4-diethylaminosulfonyl-piperazin-1-yl)sydnonimine
N⁶-(p-chloro)benzoyl-3-thiomorpholinosydnonimine
N⁶-(8-methoxy-1-naphthyl)carbonyl-3-(tetrahydro-1,4-thiazin-4-yl 1-oxide)sydnonimine
N⁶-(p-methoxy)benzoyl-3-(4-methanesulfonyl-piperazin-1-yl)sydnonimine
N⁶-(4-methyl-2-naphthyl)carbonyl-3-(4-phenylsulfonyl-piperazin-1-yl)sydnonimine
N⁶-(2,4-dibromo)benzoyl-3-[4-(p-chlorophenylsulfonyl)piperazin-1-yl]sydnonimine
N⁶-(o-toluyl)-4-bromo-3-(tetrahydro-1,4-thiazin-4-yl 1-oxide)sydnonimine
N⁶-(5-ethoxy-2-naphthyl)carbonyl-4-chloro-3-(tetrahydro-1,4-thiazin-4-yl 1,1-dioxide)sydnonimine
N⁶-(m-toluyl)-4-bromo-3-(4-ethanesulfonyl-piperazin-1-yl)sydnonimine
N⁶-(p-toluyl)-4-chloro-3-[4-(2,4-dichlorophenylsulfonyl)piperazin-1-yl]sydnonimine
N⁶-(2,4-xyloyl)-4-bromo-3-(4-diethylaminosulfonyl-piperazin-1-yl)sydnonimine
N⁶-phenacetyl-3-thiomorpholinosydnonimine
N⁶-benzylacetyl-3-(tetrahydro-1,4-thiazin-4-yl 1-oxide)-sydnonimine
N⁶-cinnamoyl-3-(tetrahydro-1,4-thiazin-4-yl 1,1-dioxide)sydnonimine
B⁶-(α-naphthyl)acetyl-3-(4-methanesulfonyl-piperazin-1-yl)sydnonimine
N⁶-phenacetyl-3-(4-phenylsulfonyl-piperazin-1-yl)sydnonimine
N⁶-cinnamoyl-4-bromo-3-(tetrahydro-1,4-thiazin-4-yl 1-oxide)sydnonimine
N⁶-(β-naphthyl)acetyl-4-chloro-3-(tetrahydro-1,4-thiazin-4-yl 1,1-dioxide)sydnonimine
N⁶-phenacetyl-4-bromo-3-(4-ethanesulfonyl-piperazin-1-yl)sydnonimine
N⁶-cinnamoyl-4-chloro-3-[4-(2,4-dichlorophenylsulfonyl)piperazin-1-yl]sydnonimine $N^6$-phenacetyl-4-bromo-3-(4-diethylaminosulfonyl-piperazin-1-yl)sydnonimine
$N^6$-methoxycarbonyl-3-(4-phenylsulfonyl-piperazin-1-yl)sydnonimine
$N^6$-isopropoxycarbonyl-4-bromo-3-(tetrahydro-1,4-thiazin-4-yl 1-oxide)sydnonimine
$N^6$-ethoxycarbonyl-4-chloro-3-[4-(2,4-dichlorophenylsulfonyl)-piperazin-1-yl]sydnonimine
$N^6$-propoxycarbonyl-4-bromo-3-(4-diethylaminosulfonyl-piperazin-1-yl)sydnonimine
$N^6$-phenoxycarbonyl-3-thiomorpholinosydnonimine
$N^6$-(α-naphthyl)oxycarbonyl-3-(tetrahydro-1,4-thiazin-4-yl 1-oxide)sydnonimine
$N^6$-phenoxycarbonyl-3-(4-methanesulfonyl-piperazin-1-yl)sydnonimine
$N^6$-(β-naphthyl)oxycarbonyl-3-(4-phenylsulfonyl-piperazin-1-yl)sydnonimine
$N^6$-phenoxycarbonyl-3-[4-(p-chlorophenylsulfonyl)piperazin-1-yl]sydnonimine
$N^6$-(α-naphthyl)oxycarbonyl-3-[4-(N-ethyl-N-methylaminosulfonyl)-piperazin-1-yl]sydnonimine
$N^6$-(β-naphthyl)oxycarbonyl-4-bromo-3-(tetrahydro-1,4-thiazin-4-yl 1-oxide)sydnonimine
$N^6$-phenoxycarbonyl-4-chloro-3-(tetrahydro-1,4-thiazin-4-yl 1,1-dioxide)sydnonimine
$N^6$-(α-naphthyl)oxycarbonyl-4-bromo-3-(4-ethanesulfonyl-piperazin-1-yl)sydnonimine
$N^6$-(β-naphthyl)oxycarbonyl-4-chloro-3-[4-(2,4-dichlorophenylsulfonyl)piperazin-1-yl]sydnonimine
$N^6$-phenoxycarbonyl-4-bromo-3-(4-diethylaminosulfonyl-piperazin-1-yl)sydnonimine
$N^6$-pyrroyl-3-thiomorpholinosydnonimine
$N^6$-(2-imidazolyl)carbonyl-3-(tetrahydro-1,4-thiazin-4-yl 1-oxide)sydnonimine
$N^6$-furoyl-3-(4-phenylsulfonyl-piperazin-1-yl)sydnonimine
$N^6$-(1-pyrazolyl)carbonyl-3-[4-(p-chlorophenylsulfonyl)piperazin-1-yl]sydnonimine
$N^6$-(3-thiazyl)carbonyl-3-[4-(N-ethyl-N-methylaminosulfonyl)-piperazin-1-yl]sydnonimine
$N^6$-(2-oxazolyl)carbonyl-4-bromo-3-(tetrahydro-1,4-thiazin-4-yl 1-oxide)sydnonimine
$N^6$-(2-thienyl)carbonyl-4-chloro-3-(tetrahydro-1,4-thiazin-4-yl 1,1-dioxide)sydnonimine
$N^6$-(3-pyrrolyl)carbonyl-4-bromo-3-(4-ethanesulfonyl-piperazin-1-yl)sydnonimine
$N^6$-(2,4,5-triazolyl)carbonyl-4-chloro-3-[4-(2,4-dichlorophenylsulfonyl)piperazin-1-yl]sydnonimine
$N^6$-(3-pyrazolyl)carbonyl-4-bromo-3-(4-diethylaminosulfonyl-piperazin-1-yl)sydnonimine
$N^6$-nicotinoyl-3-thiomorpholinosydnonimine
$N^6$-pyrazinylcarbonyl-3-(tetrahydro-1,4-thiazin-4-yl 1-oxide)sydnonimine
$N^6$-(2-pyrimidinyl)carbonyl-3-(tetrahydro-1,4-thiazin-4-yl 1,1-dioxide)sydnonimine
$N^6$-(3-pyridazinyl)carbonyl-3-(4-methanesulfonyl-piperazin-1-yl)sydnonimine
$N^6$-nicotinoyl-3-(4-phenylsulfonyl-piperazin-1-yl)sydnonimine
$N^6$-pyrazinylcarbonyl-3-[4-(p-chlorophenylsulfonyl)-piperazin-1-yl]sydnonimine
$N^6$-(2,4,6-triazinyl)carbonyl-3-[4-(N-ethyl-N-methylaminosulfonyl)piperazin-1-yl]sydnonimine
$N^6$-nicotinoyl-4-bromo-3-(tetrahydro-1,4-thiazin-4-yl 1-oxide)sydnonimine
$N^6$-(3-pyridazinyl)carbonyl-4-chloro-3-(tetrahydro-1,4-thiazin-4-yl 1,1-dioxide)sydnonimine
$N^6$-nicotinoyl-4-bromo-3-(4-ethanesulfonyl-piperazin-1-yl)sydnonimine
$N^6$-(2-pyrimidinyl)carbonyl-4-chloro-3-[4-(2,4-dichlorophenylsulfonyl)piperazin-1-yl]sydnonimine
$N^6$-nicotinoyl-4-bromo-3-(4-diethylaminosulfonyl-piperazin-1-yl)sydnonimine
$N^6$-methoxycarbonylcarbonyl-3-thiomorpholinosydnonimine
$N^6$-ethoxycarbonylcarbonyl-3-(tetrahydro-1,4-thiazin-4-yl 1-oxide)sydnonimine
$N^6$-propoxycarbonylcarbonyl-3-(4-phenylsulfonyl-piperazin-1-yl)sydnonimine
$N^6$-methoxycarbonylcarbonyl-3-[4-(p-chlorophenylsulfonyl)piperazin-1-yl]sydnonimine
$N^6$-ethoxycarbonylcarbonyl-3-[4-(N-ethyl-N-methylaminosulfonyl)-piperazin-1-yl]sydnonimine
$N^6$-ethoxycarbonylcarbonyl-4-bromo-3-(tetrahydro-1,4-thiazin-4-yl 1-oxide)sydnonimine
$N^6$-propoxycarbonyl-4-chloro-3-(tetrahydro-1,4-thiazin-4-yl 1,1-dioxide)sydnonimine
$N^6$-methoxycarbonylcarbonyl-4-bromo-3-(4-ethanesulfonyl-piperazin-1-yl)sydnonimine
$N^6$-methoxycarbonylcarbonyl-4-chloro-3-[4-(2,4-(dichlorophenylsulfonyl)piperazin-1-yl]sydnonimine
$N^6$-ethoxycarbonylcarbonyl-4-bromo-3-(4-diethylaminosulfonyl-piperazin-1-yl)sydnonimine
$N^6$-methylsulfonyl-3-thiomorpholinosydnonimine
$N^6$-ethylsulfonyl-3-(tetrahydro-1,4-thiazin-4-yl 1-oxide)sydnonimine
$N^6$-propylsulfonyl-3-(tetrahydro-1,4-thiazin-4-yl 1,1-dioxide)sydnonimine
$N^6$-allylsulfonyl-3-(4-methanesulfonyl-piperazin-1-yl)sydnonimine
$N^6$-butylsulfonyl-3-(4-phenylsulfonyl-piperazin-1-yl)sydnonimine
$N^6$-isopropylsulfonyl-3-[4-(p-chlorophenylsulfonyl)piperazin-1-yl]sydnonimine
$N^6$-butylsulfonyl-3-[4-(N-ethyl-N-methylaminosulfonyl)piperazin-1-yl]sydnonimine
$N^6$-isobutylsulfonyl-4-bromo-3-(tetrahydro-1,4-thiazin-4-yl 1-oxide)sydnonimine
$N^6$-ethylsulfonyl-4-chloro-3-(tetrahydro-1,4-thiazin-4-yl 1,1-dioxide)sydnonimine
$N^6$-amylsulfonyl-4-bromo-3-(4-ethanesulfonyl-piperazin-1-yl)sydnonimine
$N^6$-methylsulfonyl-4-chloro-3-[4-(2,4-dichlorophenylsulfonyl)-piperazin-1-yl]sydnonimine
$N^6$-allylsulfonyl-4-bromo-3-(4-diethylaminosulfonyl-piperazin-1-yl)sydnonimine
$N^6$-phenylsulfonyl-3-thiomorpholinosydnonimine
$N^6$-(α-naphthyl)sulfonyl-3-(tetrahydro-1,4-thiazin-4-yl 1-oxide)sydnonimine
$N^6$-phenylsulfonyl-3-(tetrahydro-1,4-thiazin-4-yl 1,1-dioxide)sydnonimine
$N^6$-(β-naphthyl)sulfonyl-3-(4-methanesulfonyl-piperazin-1-yl)sydnonimine
$N^6$-phenylsulfonyl-3-(4-phenylsulfonyl-piperazin-1-yl)sydnonimine
$N^6$-(α-naphthyl)sulfonyl-3-[4-(p-chlorophenylsulfonyl)-piperazin-1-yl]sydnonimine
$N^6$-phenylsulfonyl-3-[4-(N-ethyl-N-methylaminosulfonyl)piperazin-1-yl]sydnonimine
$N^6$-phenylsulfonyl-4-bromo-3-(tetrahydro-1,4-thiazin-4-yl 1-oxide)sydnonimine
$N^6$-(α-naphthyl)sulfonyl-4-chloro-3-(tetrahydro-1,4-thiazin-4-yl 1,1-dioxide)sydnonimine
$N^6$-phenylsulfonyl-4-bromo-3-(4-ethanesulfonyl-piperazin-1-yl)sydnonimine $N^6$-phenylsulfonyl-4-chloro-3-[4-(2,4-dichlorophenylsulfonyl)-piperazin-1-yl]sydnonimine
$N^6$-(α-naphthyl)sulfonyl-4-bromo-3-(4-diethylaminosulfonyl-piperazin-1-yl)sydnonimine
$N^6$-(p-chlorophenyl)sulfonyl-3-thiomorpholinosydnonimine
$N^6$-(p-tolyl)sulfonyl-3-(tetrahydro-1,4-thiazin-4-yl 1-oxide)sydnonimine
$N^6$-(8-methoxy-1-naphthyl)sulfonyl-3-(4-phenylsulfonyl-piperazin-1-yl)sydnonimine
$N^6$-(p-methoxyphenyl)sulfonyl-3-[4-(p-chlorophenylsulfonyl)-piperazin-1-yl]sydnonimine
$N^6$-(4-methyl-2-naphthyl)sulfonyl-3-[4-(N-ethyl-N-methylaminosulfonyl)piperazin-1-yl]sydnonimine
$N^6$-(4,5-dichloro-1-naphthyl)sulfonyl-4-bromo-3-(tetrahydro-1,4-thiazin-4-yl)sydnonimine
$N^6$-(o-tolyl)sulfonyl-4-chloro-3-(tetrahydro-1,4-thiazin-4-yl 1,1-dioxide)sydnonimine
$N^6$-(5-ethoxy-2-naphthyl)sulfonyl-4-bromo-3-(4-ethanesulfonyl-piperazin-1-yl)sydnonimine
$N^6$-(2,4-dimethoxyphenyl)sulfonyl-4-chloro-3-[4-(2,4-dichlorophenylsulfonyl)piperazin-1-yl]sydnonimine
$N^6$-(p-tolyl)sulfonyl-4-bromo-3-(4-diethylaminosulfonyl-piperazin-1-yl)sydnonimine
$N^6$-dimethylaminosulfonyl-3-thiomorpholinosydnonimine
$N^6$-(N-ethyl-N-methyl)aminosulfonyl-3-(tetrahydro-1,4-thiazin-4-yl 1-oxide)sydnonimine
$N^6$-diethylaminosulfonyl-3-(tetrahydro-1,4-thiazin-4-yl 1,1-dioxide)sydnonimine
$N^6$-diamylaminosulfonyl-3-(4-methanesulfonyl-piperazin-1-yl)sydnonimine
$N^6$-dipropylaminosulfonyl-3-(4-phenylsulfonyl-piperazin-1-yl)sydnonimine
$N^6$-(N-methyl-N-propyl)aminosulfonyl-3-[4-(p-chlorophenylsulfonyl)piperazin-1-yl]sydnonimine
$N^6$-diisopropylaminosulfonyl-3-[4-(N-ethyl-N-methylaminosulfonyl)piperazin-1-yl]sydnonimine
$N^6$-dibutylaminosulfonyl-4-bromo-3-(tetrahydro-1,4-thiazin-4-yl 1-oxide)sydnonimine
$N^6$-diethylaminosulfonyl-4-chloro-3-(tetrahydro-1,4-thiazin-4-yl 1,1-dioxide)sydnonimine
$N^6$-dihexylaminosulfonyl-4-bromo-3-(4-ethanesulfonyl)-piperazin-1-yl)sydnonimine
$N^6$-dimethylaminosulfonyl-4-chloro-3-[4-(2,4-dichlorophenylsulfonyl)piperazin-1-yl]sydnonimine
$N^6$-(N-ethyl-N-methyl)aminosulfonyl-4-bromo-3-(4-diethylaminosulfonyl-piperazin-1-yl)sydnonimine Illustrative of corresponding intermediates of formula II (analogously prepared from equivalents of corresponding starting materials, as hereinbefore described) are:

N-nitroso-N-thiomorpholino-cyanomethylamine
N-nitroso-N-(tetrahydro-1,4-thiazin-4-yl 1-oxide)-cyanomethylamine
N-nitroso-N-(tetrahydro-1,4-thiazin-4-yl 1,1-dioxide)-cyanomethylamine
N-nitroso-N-(4-methanesulfonyl-piperazin-1-yl)-cyanomethylamine
N-nitroso-N-(4-phenylsulfonyl-piperazin-1-yl)-cyanomethylamine
N-nitroso-N-(4-tosyl-piperazin-1-yl)-cyanomethylamine
N-nitroso-N-(4-dimethylaminosulfonyl-piperazin-1-yl)-cyanometylamine The examples which follow serve to illustrate the invention in more detail; in these examples percentage data are percentages by weight unless otherwise stated.

EXAMPLE 1

3-Thiomorpholino-sydnonimine hydrochloride 17.7 g of aminothiomorpholine are dissolved in 100 g of water. The pH value of the resulting solution is adjusted to 4 by adding concentrated hydrochloric acid dropwise; the solution is then cooled to from 0° to 5° C., and a solution of 7.4 g of sodium cyanide in 15 g of water is added dropwise thereto. After adding 12.4 g of 40% strength formalin, the solution is left to stand overnight (pH=7 to 7.5). The pH value is then adjusted to 2 with concentrated hydrochloric acid. The solution is subsequently cooled to 0° C., and a solution of 10.4 g of sodium nitrite in 30 g of water is slowly added dropwise; the resulting mixture is stirred for a further 1 hour at from 0° to 5° C. and then extracted twice with 50 ml of ethyl acetate (each time). The thus obtained organic phase is dried over sodium sulfate. After diluting the resulting solution with 150 ml of methanol, 15 g of hydrogen chloride are passed in, with water-cooling, and the resulting mixture is stirred for a further 1 hour. The solid product is then filtered off. The mother liquor is concentrated, and the product [melting point: 181° to 183° C. (decomposition); yield: 18.5 g (83% of theory)] is recrystallized from ethanol.

Following the same procedure and replacing the aminothiomorpholine by an equivalent of each of: 4-aminotetrahydro-1,4-thiazine dioxide, 4-amino-tetrahydro-1,4-thiazine oxide, 1-amino-4-methanesulfonyl-piperazine, 1-amino-4-dimethylaminosulfonyl-piperazine and 1-amino-4-tosylpiperazine, respectively, results in the synthesis of the following compounds according to the invention: 3-(tetrahydro-1,4-thiazin-4-yl 1,1-dioxide)sydnonimine hydrochloride, melting point: 206° to 208° C. (with decomposition); 3-(tetrahydro-1,4-thiazin-4-yl 1-oxide)sydnonimine hydrochloride, melting point: 200° to 201° C. (with decomposition); 3-(4-methanesulfonyl-piperazin-1-yl)sydnonimine hydrochloride, melting point: 226° C. (with decomposition); 3-[4-(p-toluenesulfonyl)piperazin-1-yl]sydnonimine hydrochloride, melting point: 212° C. (with decomposition); and 3-[4-dimethylaminosulfonyl)piperazin-1-yl]sydnonimine hydrochloride, melting point: 193° to 194° C. (with decomposition), respectively.

The 1-amino-4-methanesulfonyl-piperazine required as a starting material is synthesized, e.g., as follows:

10 g of methanesulfonyl-piperazine are dissolved in 50 ml of water; after adding 6.2 ml of concentrated hydrochloric acid thereto, a solution of 5.4 g of potassium cyanate in 20 ml of water is added dropwise, and the thus-obtained mixture is stirred for 4 hours at room temperature. The precipitate which separates out is filtered off and dried. Yield: 11 g; melting point: 254° C. 10 g of the dried precipitate and 4 g of sodium hydroxide solution in 80 ml of water are cooled to 0° C., and 0.052 mol of sodium hypochlorite, which has been pre-cooled to 0° C., is added. The mixture is then stirred at room temperature until no further hypochlorite is detectable. The aqueous solution of 1-aminomethanesulfonylpiperazine, which is obtained in this way, is directly useful in the further reaction.

Other starting materials of the piperazine series are analogously prepared.

EXAMPLE 2

3-(Tetrahydro-1,4-thiazin-4-yl 1-oxide)sydnonimine hydrochloride 17.5 g of 3-thiomorpholinosydnonimine hydrochloride are dissolved in 100 ml of glacial acetic acid. 9.0 g of an aqueous 30% strength hydrogen peroxide solution are added dropwise to this solution, and the resulting mixture is stirred for one hour at room temperature. After concentrating in vacuo, the product [melting point: 200° to 201° C. (with decomposition), yield: 15.3 g (86% of theory)] is recrystallized from ethanol.

3-(Tetrahydro-1,4-thiazin-4-yl 1,1-dioxide)sydnonimine hydrochloride is synthesized analogously to this example by using a larger excess of 30% strength hydrogen peroxide and by using more severe reaction conditions.

EXAMPLE 3

$N^6$-Acetyl-3-thiomorpholinosydnonimine hydrochloride 6.0 g of 3-thiomorpholinosydnonimine hydrochloride are suspended in 50 ml of acetic anhydride. After adding 10 ml of anhydrous pyridine thereto, the mixture is stirred overnight. The thus-obtained colorless crystals are filtered off and recrystallized from methanol to produce the title compound [melting point: 197° C. (with decomposition); yield: 6.3 g (89% of theory)].

From equivalents of corresponding starting materials the following compounds according to the invention are prepared analogously to this example: $N^6$-acetyl-3-(tetrahydro-1,4-thiazin-4-yl 1,1-dioxide)sydnonimine, melting point: 212° to 214° C. (with decomposition); $N^6$-methoxyacetyl-3-(tetrahydro-1,4-thiazin-4-yl 1,1-dioxide)sydnonimine, melting point: 188° to 192° C. (with decomposition); $N^6$-acetyl-3-(4-dimethylaminosulfonyl-piperazin-1-yl)sydnonimine hydrochloride, melting point: 185° C. (with decomposition); $N^6$-acetyl-3-(4-dimethylaminosulfonyl-piperazin-1-yl)sydnonimine, melting point: 176° to 177° C. (with decomposition); $N^6$-acetyl-3-(4-methanesulfonyl-piperazin-1-yl)sydnonimine hydrochloride, melting point: 204° C. (with decomposition); $N^6$-acetyl-3-(4-methanesulfonyl-piperazin-1-yl)sydnonimine, melting point: 236° C. (with decomposition); $N^6$-propionyl-3-(4-dimethylaminosulfonyl-piperazin-1-yl)sydnonimine hydrochloride, melting point: 179° C. (with decomposition); and $N^6$-formyl-3-(tetrahydro-1,4-thiazin-4-yl 1,1-dioxide)sydnonimine, melting point: 213° C. (with decomposition).

EXAMPLE 4

$N^6$-Pivaloyl-3-(4-methanesulfonyl-piperazin-1-yl)sydnonimine 28.3 g of 3-(4-methanesulfonyl-piperazin-1-yl)sydnonimine hydrochloride are dissolved in 200 ml of water. The resulting solution is cooled to 0° C., and 28 g of sodium bicarbonate are added thereto while stirring. 24 g of pivaloyl chloride are then added, and the solution is stirred overnight at room temperature. The thus-obtained solid compound is filtered off and recrystallized from ethanol to obtain the title compound [melting point: 94° to 95° C.; yield: 25.8 g (78% of theory)].

This compound is conventionally converted to its hydrochloride, which has a melting point of 178° C. (with decomposition), by dissolving it in methanol and adding methanolic hydrochloric acid to the resulting solution.

EXAMPLE 5

$N^6$-Benzoyl-3-(4-methanesulfonyl-piperazin-1-yl)sydnonimine 5.6 g of 3-(4-methanesulfonyl-piperazin-1-yl)sydnonimine hydrochloride and 2.8 g of benzoyl chloride are stirred in 50 ml of anhydrous pyridine for one day at room temperature. The resulting fine, crystalline precipitate is filtered off and recrystallized from ethanol to obtain the title compound [melting point: 225° C. (with decomposition); yield: 6.0 g (85% of theory)].

From equivalents of corresponding starting materials the following compounds according to the invention are prepared analogously to examples 4 and 5: $N^6$-ethoxycarbonyl-3-(tetrahydro-1,4-thiazin-4-yl 1,1-dioxide)sydnonimine, melting point: 208° to 210° C. (with decomposition); $N^6$-cyclohexylcarbonyl-3-(tetrahydro-1,4-thiazin-4-yl 1,1-dioxide)sydnonimine, melting point: 160° to 163° C.; $N^6$-ethoxycarbonyl-3-thiomorpholinosydnonimine, melting point: 166° to 168° C.; $N^6$-ethoxycarbonyl-3-(tetrahydro-1,4-thiazin-4-yl 1-oxide)sydnonimine, melting point: 135° C.; $N^6$-(p-chlorobenzoyl)-3-tetrahydro-1,4-thiazin-4-yl 1,1-dioxide)sydnonimine, melting point: 248° to 249° C. (with decomposition); $N^6$-phenoxycarbonyl-3-(tetrahydro-1,4-thiazin-4-yl 1,1-dioxide)sydnonimine, melting point: 213° to 215° C. (with decomposition); $N^6$-cinnamoyl-3-(4-dimethylaminosulfonyl-piperazin-1-yl)sydnonimine, melting point: 190° to 192° C.; $N^6$-benzoyl-3-(tetrahydro-1,4-thiazin-4-yl 1,1-dioxide)sydnonimine, melting point: 245° to 247° C. (with decomposition); $N^6$-ethoxycarbonyl-3-[4-(p-toluenesulfonyl)-piperazin-1-yl]sydnonimine, melting point: 190° to 192° C.; $N^6$-cyclohexylcarbonyl-3-(4-methanesulfonyl-piperazin-1-yl)sydnonimine, melting point: 171° to 172° C. (with decomposition); $N^6$-phenoxyacetyl-3-[4-(p-toluenesulfonyl)-piperazin-1-yl]sydnonimine, melting point: 150° C. (with decomposition); $N^6$-pivaloyl-3-(tetrahydro-1,4-thiazin-4-yl 1,1-dioxide)sydnonimine, melting point: 183° C. (with decomposition); $N^6$-(3,4,5-trimethoxybenzoyl)-3-(tetrahydro-1,4-thiazin-4-yl 1,1-dioxide)sydnonimine, melting point: 188° C.; $N^6$-ethoxycarbonyl-3-(4-methanesulfonyl-piperazin-1-yl)sydnonimine, melting point: 194° C. (with decomposition); $N^6$-ethoxycarbonylcarbonyl-3-(tetrahydro-1,4-thiazin-4-yl 1,1-dioxide)sydnonimine, melting point: 179° to 181° C.; $N^6$-neopentylcarbonyl-3-(tetrahydro-1,4-thiazin-4-yl 1,1-dioxide)sydnonimine, melting point: 168° to 171° C.; $N^6$-ethoxycarbonyl-3-(4-dimethylaminosulfonyl-piperazin-1-yl)sydnonimine, melting point: 167° to 168° C.; $N^6$-nicotinoyl-3-(4-methanesulfonyl-piperazin-1-yl)sydnonimine, melting point: 206° to 207° C.; $N^6$-nicotinoyl-3-(tetrahydro-1,4-thiazin-4-yl 1,1-dioxide)sydnonimine, melting point: 235° C. (with decomposition); $N^6$-(2,4-dichlorobenzoyl)-3-(4-dimethylaminosulfonyl-piperazin-1-yl)sydnonimine, melting point: 194° to 196° C.; $N^6$-ethoxycarbonylcarbonyl-3-(4-methanesulfonyl-piperazin-1-yl)sydnonimine, melting point: 182° C. (with decomposition); $N^6$-benzoyl-3-(4-dimethylaminosulfonyl-piperazin-1-yl)sydnonimine, melting point: 205° to 207° C.; $N^6$-phenylacetyl-3-(4-tosyl-piperazin-1-yl)sydnonimine, melting point: 160° C.; $N^6$-butoxyacetyl-3-(4-tosyl-piperazin-1-yl)sydnonimine, melting point: 119° to 121° C.; $N^6$-tosyl-3-(4-methanesulfonyl-piperazin-1-yl)sydnonimine, melting point: 250° C. (with decomposition); and N⁶-tosyl-3-(tetrahydro-1,4-thiazin-4-yl 1,1-dioxide)sydnonimine, melting point: 167° to 169° C.

EXAMPLE 6

N⁶-Nitroso-3-(tetrahydro-1,4-thiazin-4-yl 1,1-dioxide)sydnonimine 5.1 g of 3-(tetrahydro-1,4-thiazin-4-yl 1,1-dioxide)-sydnonimine hydrochloride are dissolved in 30 ml of water. After cooling to form 0° to 5° C., a solution of 1.4 g of sodium nitrite in 15 ml of water is added dropwise thereto, the mixture is stirred for a further one hour at 5° C. and the thus-obtained title product [melting point: 128° to 130° C. (with decomposition); yield: 3.9 g (78% of theory)] is filtered off.

EXAMPLE 7

N⁶-Ethoxycarbonyl-3-(4-methanesulfonyl-piperazin-1-yl)-4-bromosydnonimine 3.2 g of N⁶-ethoxycarbonyl-3-(4-methanesulfonyl-piperazin-1-yl)sydnonimine are suspended in 40 ml of carbon tetrachloride. 3.2 g of N-bromosuccinimide are introduced in small portions, and the resulting mixture is then heated at from 50° to 60° C. and stirred vigorously for 30 minutes. After cooling with ice-water, obtained colorless crystals are filtered off and recrystallized from methanol to produce the title compound [melting point: 120° to 122° C. (with decomposition); yield: 3.0 g (63% of theory)].

N⁶-Ethoxycarbonyl-3-(tetrahydro-1,4-thiazin-4-yl 1,1-dioxide)-4-bromosydnonimine [melting point: 160° to 164° C. (with decomposition) is analogously obtained.

The invention and its advantages are readily understood from the foregoing description. Various changes can be made in the final products, the intermediates, the synthesis, the compositions and the method of use without departing from the spirit and scope of the invention or sacrificing its material advantages. The described compounds, syntheses, compositions and methods of use are merely illustrative of embodiments of the invention.

EXAMPLE 8

Sugar-coated pills can be prepared according to the following formulations:

| | |
|---|---|
| 3-(tetrahydro-1,4-thiazin-4-yl-1,1 dioxide)-sydnonimine hydrochloride | 1 mg |
| cornstarch | 100 mg |
| lactose | 60 mg |
| sec. calcium phosphate | 30 mg |
| soluble starch | 3 mg |
| magnesium stearate | 2 mg |
| colloidal silicic acid | 4 mg |
| | 200 mg |

EXAMPLE 9

Tablets can be prepared according to the following formulations:

| | |
|---|---|
| N⁶-benzoyl-3-(4-methanesulfonyl-piperazine-1-yl)-sydnonimine | 2 mg |
| lactose | 60 mg |
| cornstarch | 30 mg |
| soluble starch | 4 mg |
| magnesium stearate | 4 mg |

-continued

| | |
|---|---|
| | 100 mg |

What is claimed is:

1. A compound which, in its free-base form, is a pharmacologically-active and physiologically-acceptable 3-amino-sydnonimine of the formula

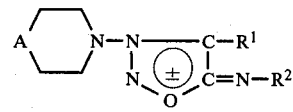

wherein
R¹ is —H or halo;
R² is —H, —NO, —COR³ or SO₂R⁴;
R³ is —H; optionally-substituted aliphatic hydrocarbyl having from 1 to 6 carbon atoms and any substituent of which is alkoxy with from 1 to 6 carbon atoms or carbocyclic aryloxy with from 6 to 12 carbon atoms; cycloaliphatic hydrocarbyl having from 5 to 8 ring carbon atoms; optionally-substituted carbocyclic aryl with from 6 to 12 ring carbon atoms and 0, 1, 2 or 3 substituents, any of which is, independently, halo, alkyl with from 1 to 4 carbon atoms or alkoxy with from 1 to 4 carbon atoms; araliphatic hydrocarbyl with from 7 to 13 carbon atoms; alkoxy with from 1 to 6 carbon atoms; carbocyclic aryloxy with from 6 to 12 carbon atoms; heteroaryl with 5 or 6 ring members, at least 2 of which are carbon atoms, at most one of which is a sulfur atom, at most one of which is an oxygen atom and at most three of which are nitrogen atoms, and wherein any ring member is a carbon atoms, a sulfur atom, an oxygen atom or a nitrogen atom; or alkoxycarbonyl with from 2 to 7 carbon atoms;
A is >S and
R⁴ is aliphatic hydrocarbyl with from 1 to 6 carbon atoms; optionally-substituted carbocyclic aryl with from 6 to 12 ring carbon atoms, any substituent of which is methyl or chloro; or dialkylamino, each alkyl of which has, independently, from 1 to 4 carbon atoms.

2. A free base according to claim 1.

3. A physiologically-acceptable acid-addition salt according to claim 1.

4. A compound according to claim 1 wherein R¹ is —H.

5. A compound according to claim 4 wherein R² is —H.

6. A compound according to claim 1 wherein R² is —COR³ and R³ is alkyl with from 1 to 4 carbon atoms.

7. A compound according to claim 6 wherein R¹ is —H.

8. A compound according to claim 1 wherein R² is —H.

9. A compound according to claim 1 wherein R² is —CO-pyridyl.

10. A compound according to claim 1 or 4 wherein R² is —CO—OCH₃ or —CO—O—CH₂CH₃.

11. A compound according to claim 1 or 4 wherein R² is —COR³, and R³ is alkoxycarbonyl with a total of 2 or 3 carbon atoms.

12. A compound according to claim 1 wherein R¹ is —H, and R² is —H.

13. A compound according to claim 1 wherein $R^2$ is —$COR^3$.

14. A compound according to claim 13 wherein $R^3$ is cycloaliphatic hydrocarbyl.

15. A compound according to claim 13 wherein $R^3$ is optionally-substituted carbocyclic aryl.

16. A compound according to claim 13 wherein $R^3$ is alkoxycarbonyl.

17. A compound according to claim 1 wherein $R^1$ is H.

18. A pharmaceutical composition useful for reducing blood pressure, in unit-dosage form and having from 0.1 to 50 milligrams of a pharmacologically-acceptable compound according to claim 1 in combination with carrier therefor.

19. A pharmaceutical composition for reducing blood pressure and having, per unit dose, an effective amount of a pharmacologically-acceptable compound according to claim 1 in combination with suitable carrier.

20. A pharmaceutical composition according to claim 19 comprising at least one additional pharmaceutically-active compound.

21. A method of reducing cardiac work (in the sense of an anti-anginal action) without provoking reflex tachycardia which comprises administering to a patient in need of such action an effective amount of a composition according to claim 20.

22. A method according to claim 21 which comprises orally administering the pharmaceutical composition.

* * * * *